United States Patent [19]
Speck

[11] Patent Number: 5,451,509
[45] Date of Patent: Sep. 19, 1995

[54] COAGULATION ASSAYS AND REAGENTS

[75] Inventor: Roy E. Speck, Indianapolis, Ind.

[73] Assignee: Analytical Control Systems, Inc., Fishers, Ind.

[21] Appl. No.: 158,538

[22] Filed: Nov. 29, 1993

Related U.S. Application Data

[60] Division of Ser. No. 946,811, Sep. 16, 1992, abandoned, which is a continuation of Ser. No. 510,178, Apr. 17, 1990, abandoned.

[51] Int. Cl.$^6$ .......................... C12Q 1/56; G01N 33/86
[52] U.S. Cl. ........................................ 435/13; 436/69
[58] Field of Search ............................ 435/13; 436/69; 514/730, 724

[56] References Cited

U.S. PATENT DOCUMENTS

| | | | |
|---|---|---|---|
| 3,486,981 | 12/1969 | Speck | 435/13 |
| 4,455,377 | 6/1984 | Finnerty et al. | 435/13 |
| 4,666,831 | 5/1987 | Janoff et al. | 435/13 |
| 4,732,860 | 3/1988 | Bartl et al. | 435/13 |
| 4,985,354 | 1/1991 | Toyomaki et al. | 435/13 |
| 5,039,617 | 8/1991 | McDonald et al. | 435/13 |
| 5,055,412 | 10/1991 | Proksch | 435/13 |
| 5,091,304 | 2/1992 | LaDuca et al. | 435/13 |

FOREIGN PATENT DOCUMENTS

| | | |
|---|---|---|
| 29 15 310.4 | of 0000 | Germany . |
| 9011368 | 10/1990 | WIPO . |
| 9116453 | 10/1991 | WIPO . |

OTHER PUBLICATIONS

A. Girolami et al., "Failure of Ellagic Acid to Affect Platelet Aggregation in Normal and in Facot XII Deficient Plasma", *Blut*, 31, 1975, pp. 107–112.

R. E. Speck, "Accurate Assays for Platelet Factor 3", *American Clinical Laboratory*, 12(9), 1993, pp. 16–18.

M. H. Kroll et al., "Biochemical Mechanisms of Platelet Activation", *Blood*, 74(4), 1989, pp. 1181–1195.

E. W. Salzman et al., "Effect of Heparin and Heparin Fractions on Platelet Aggregation", *Journal of Clinical Investigations*, 65, 1980, pp. 64–73.

J. D. Sweeney et al., "The Effect of the Platelet Count on the Aggregation Response and Adenosine Triphosphate Release in an Impedance Lumi-Aggregometer", *American Journal of Clinical Pathology*, 89, 1988, pp. 655–659.

J. D. Sweeney et al., "Ristocetin-Induced Platelet Aggregate Formation and Adherence to the Probe of an Impedance Aggregometer", *American Journal of Clincal Pathology*, 93, 1990, pp. 548–551.

C. E. Isenhart, "Platelet Aggregation Studies for the Diagnosis of Heparin-Induced Thrombocytopenia", *American Journal of Clinical Pathology*, 1993, pp. 324–330.

(List continued on next page.)

*Primary Examiner*—Michael G. Wityshyn
*Assistant Examiner*—Timothy J. Reardon
*Attorney, Agent, or Firm*—Kenyon & Kenyon

[57] ABSTRACT

Novel assays and reagents for determining coagulative properties of blood or plasma are disclosed, as are agents and methods for stemming bleeding. Novel ellagic acid-based activators consist essentially of aqueous solutions of ellagic acid, phenol and suitable metal ions and give defined values for a novel platelet assay also disclosed. Inventive coagulation reagents including propyl gallate or tannin are also disclosed, as are aPTT reagents having sensitivity to heparin and Factor deficiencies far superior to prior aPTT reagents. Disclosed heparin-sensitive reagents include dextran sulfate. Also disclosed is applicant's discovery that reagents including hydroxy-substituted compounds and metal ions, heretofore known to activate Hagemann Factor, also cause platelets to release Platelet Factor 3, and a series of platelet-sensitive tests found to be enabled by this discovery. These platelet-sensitive tests include assays for platelet activity, systemic lupus, platelet reserve, which can signify type II lipoprotein defects, and for Platelet Factor 4. Disclosed methods and materials for stemming bleeding center around applicant's discovery that bleeding from bleeding sites can be stopped up to six times faster by applying to the site a hemostatic agent including effective amounts of hydroxy-substituted aromatic compound and metal ion.

4 Claims, 5 Drawing Sheets

OTHER PUBLICATIONS

Y. S. Arkel, "Evaluation of Platelet Aggregation in Disorders of Hemostasis", *Medical Clinics of North America*, 60, 1976, pp. 881–911.

R. M. Hardisty et al., "The Kaolin Clotting Time of Platelet Rich Plasma: A Test of Platelet Factor 3 Availability", *British Journal of Haematology*, 11, 1965, pp. 258–268.

E. J. Bowie, "Standardization of Platelets in the Thromboplastin Generation Test", *The American Journal of Clinical Pathology*, 44, 1965, pp. 673–677.

R. M. Hardisty et al., "Platelet Aggregation and the Availability of Platelet Factor 3", *British Journal of Haematology*, 12, 1966, pp. 764–776.

H. Sandberg et al., "A Highly Sensitive Assay of Platelet Factor 3 Using a Chromogenic Substrate", *Thrombosis Research*, 14, 1979, pp. 113–124.

P. E. Bock et al., "Activation of Intrisic Blood Coagulation by Ellagic Acid: Insoluble Ellagic Acid–Metal Ion Complexes Are the Activating Species", *Biochemistry*, 20, 1981, pp. 7258–7266.

O. D. Ratnoff et al., "Activation of Hageman Factor by Solutions of Ellagic Acid", *The Journal of Laboratory and Clinical Medicine*, 63, 1964, pp. 359–377.

V. Dayton et al., "Laboratory Diagnosis of Lupus Anticoagulant: Comparison of Three Methods of Antibody Neutralization", *Laboratory Medicine*, Jan. 1990, pp. 30–32.

T. Exner et al., "A Sensitive Test Demonstrating Lupus Anticoagulant and its Behavioral Patterns", *British Journal of Haematology*, 40, 1978, pp. 143–151.

D. A. Triplett et al., "Laboratory Diagnosis of Lupus Inhibitors: A Comparison of the Tissue Thromboplastin Inhibition Procedure with a New Platelet Neutralization Procedure", *American Journal of Clinical Pathology*, 79, 1983, pp. 678–682.

J. Aznar et al., "Effect of Contact Factor (Factor XII + Factor XI) on Aggregation of Platelets", *Haemostasis*, 3, 1974, pp. 20–30.

G. Rouser et al., "Phospholipid Structure and Thromboplastic Activity", *Biochimica Et Biophysica Acta*, 28, 1958, pp. 71–80.

R. G. Mason et al., "Some Effects of a Microcrystalline Collagen Preparation on Blood", *Haemostasis*, 3, 1974, pp. 31–45.

A. P. Bode et al., "Analysis of Platelet Factor 3 in Platelet Concentrates Stored for Transfusion", *Vox Sanguinis*, 51, 1986, pp. 299–305.

H. D. Reuter et al., "Untersuchengen zum Einifluβ eines Wirkstoffgemisches aus Kalium-, Magnesium-, Kupfer-Mangan-und Kobaltsalzen der Asparaginsäure auf die Plättchenfaktor-3-Verfügbarkeit[1]", *Arzeneim-Forsch/Drug Research*, 30(12), 1980, pp. 2106–2108 (Translation not provided/Abstract Only).

M. Boxer et al., "The Lupus Antecoagulant", *Arthritis and Rheumatism*, 19(6), 1976, pp. 1244–1246.

J. Ramanathan et al., "Correlation Between Bleeding Times and Platelet Counts in Women with Preeclampsia Undergoing Cesarean Section", *Anesthesiology*, 71, 1989, pp. 188–191.

D. A. Triplett, *College of American Pathologists Today*, 3, 1989, p. 61.

M. A. Schleider et al., "A Clinical Study of the Lupus Anticoagulant", *Blood*, 48, 1976, pp. 449–509.

*Physician's Desk Reference*, "Avitene", pp. 588–589.

G. V. R. Born et al., "The Aggregation of Blood Platelets", *Journal of Physiology*, 168, 1963, pp. 178–194.

J. R. A. Mitchell et al., "Platelet Clumping In Vitro", *British Journal of Haematology*, 10, 1964, pp. 78–93.

N. G. Ardlie et al., "Adenosine Diphosphate–induced Platelet Aggregation in Suspensions of Washed Rabbit Platelets", *British Journal Of Haematology*, 19, 1970, pp. 7–17.

K. M. Brinkhous et al., "Macroscopic Studies of Platelet Agglutination; Nature of Thrombocyte Agglutinating Activity of Plasma", *The Proceedings of Society for Experimental Biology*, 98, 1958, pp. 379–383.

M. A. Packham et al., "Effect of Adenine Compounds on Platelet Aggregation", *American Journal of Physiology*, 217(4), 1969, pp. 1009–1017.

G. V. R. Born et al., "Effects of Inorganic Ions and of Plasma Proteins on the Aggregation of Blood Platelets by Adenosine Diphosphate", *Journal of Physiology*, 170, 1964, 397–414.

R. G. Mason et al., "Platelet Response to Six Agglutinating Agents: Species Similarities and Differences", *Experimental and Molecular Pathology*, 6, 1967, 370–381.

S. Budavari et al., *The Merck Index*, 11th edition, 1989, "Ellagic Acid", p. 3512.

R. Speck et al., "A Comparison of a Slide Platelet Aggregation Procedure with the Bleeding Time Test", *American Clinical Laboratory*, 13(1), 1994, pp. 12–13.

COAGULATION ASSAYS AND REAGENTS

This application is a division of U.S. Ser. No. 07/946,811, filed on Sep. 16. 1992 and now abandoned, which is a continuation of U.S. Ser. No. 07/510,178, filed Apr. 17, 1990, now abandoned.

BACKGROUND OF THE INVENTIONS

The present inventions relate generally to medical diagnosis and treatment, and more particularly to assays and reagents for determining coagulative properties of blood or plasma, and to agents and methods for promoting clotting.

By way of background, the ability of animals to selectively form blood clots in areas of trauma is a vital function. Failure of the blood to clot, of course, can lead to severe hemorrhage and in some instances eventual fatality. On the other hand, uncontrolled clotting or coagulation of the blood within vessels can also lead to serious complications. In light of these and other complications related to blood clotting, there has naturally been a great desire to develop tests which can be used to measure clotting tendencies and to determine the cause of any abnormalities, as well as methods and materials for treating bleeding sites. A number of tests have been developed to monitor or determine the causes of abnormal blood clotting tendencies. Although these known tests have in some instances proven acceptable to some extent, especially in light of the desire to improve the human condition, there is a continuing need for even more sensitive blood clotting tests which give consistent and reproducible results. Additionally, improvements need to be made in the reagents for these prior art tests, which are commonly turbid or include undesirable particulate matter, and which have solid, non-soluble activating species, which fact is borne out by filtering these prior art reagents and noting substantial if not complete loss of coagulation activating ability. Further, there is an ever-present need for new assays for accurately monitoring or determining clotting conditions for which there are no known accurate tests.

For example, one general coagulation test procedure which has been developed is the activated partial thromboplastin time (also commonly referred to as the aPTT), Early on, a typical aPTT test was conducted by incubating a citrated plasma sample in contact with a solid material, such as glass, celite or kaolin, known to activate Factor XII (Hagemann Factor). Then, $Ca^{2+}$ ion and a platelet substitute (i.e. a phospholipid such as a cephalin derived from brain tissue or soy bean) was added to the sample, and the time necessary for the sample to clot was measured. More recently, commercial aPTT reagents have been developed which include the platelet substitute and a chemical known to activate Hagemann Factor, such as ellagic acid. For example, commercial aPTT reagents are available from Dade Division of Baxter Travenol, of Miami, Fla., Ortho Diagnostics of Raritan, N.J., and Nyegaard A.S. of Norway. In a typical use, these commercial aPTT reagents are added to a citrated plasma sample which is then incubated for a period of time (commonly about 5 minutes) for activation to occur. $Ca^{2+}$ is then added to the sample, often in the form of $CaCl_2$, and the time necessary for clotting is measured. However, these aPTT reagents have proven to be unsatisfactory in many aspects because they are not sensitive enough to heparin, Factor deficiencies, or other causes of abnormal cloning tendencies. Also, these commercial reagents give sporadic and unreproducible results in some instances, problems which some have attributed to the presence of particulate or otherwise non-dissolved matter in the reagents. Also, the activator in these commercial reagents is not in solution, a fact which is confirmed by filtering the reagents and noting a substantial or complete loss of activating behavior.

Another generally known coagulation test procedure is the Activated Whole Blood Coagulation Time (AWBCT). Typical known AWBCT tests are performed by placing a whole blood specimen in a test tube containing solid particulate material such as celite for activation of Hagemann Factor. Thereafter, the sample is heated and agitated, and the time necessary for the sample to clot is measured. As with the known aPTT tests, however, these prior art AWBCT tests often give unreliable and unreproducible results. This could result from activation with the solid particulate material. Activation in this manner tends to be non-uniform and to interfere with normal coagulation mechanisms due to adsorption of Factors and other materials to the solid particles.

In addition to the above-noted shortcomings of known tests and reagents, there has been a more wholesale failure in this area in providing blood clotting tests which are sensitive to the activity of blood platelets in the coagulation scheme. This is despite the existence of very numerous disorders and treatments which impact platelet activity.

For example, one condition which is known to affect platelet activity is systemic lupus. This form of lupus is thought to be attributable to the presence of "lupus anticoagulant," which is an antiphospholipid antibody which inhibits the action of Platelet Factor 3 (PF3) in the coagulation mechanism. One test which has been suggested for use in detecting lupus anticoagulant is an ACT test performed on platelet poor plasma using kaolin to activate Hagemann Factor. T. Exner et al., *British Journal of Haematology*, 1978, 40, 143–51. While Exner et al. reported successfully detecting lupus anticoagulant using their method, it nonetheless involves using solid particulate material for activation which, as discussed above, can lead to decreased sensitivity and consistency from test to test.

The Tissue Thromboplastin Inhibition Procedure (TTI), M. Boxer et al., *Arthritis Rheum.* 19:1244 (1976); M. A. Schleider et al., *Blood,* 1976, 48, 499–509, and the Platelet Neutralization Procedure (PNP), D.A. Triplett et al., *A.J.C.P.,* 79, No. 6, 678–82 (June 1983), have also been suggested for use in detecting the presence of lupus anticoagulant. However, D. A. Triplett et al. demonstrated that the TTI procedure is not specific for lupus anticoagulants and thus does not provide a desirable test for detecting systemic lupus. Additionally, the PNP, while having been demonstrated to be sufficiently sensitive for qualitative determination of lupus anticoagulant, see V. Dayton et al., *Laboratory Medicine*, January 1990, pp. 30–32, does not provide a test for qualitative and quantitative study of platelet activity, and relies upon the addition of freeze-thawed platelets to neutralize the lupus anticoagulant.

In addition to detection of systemic lupus, there are also many other conditions which contribute to the need and desire for sensitive, reliable tests for platelet activity. For instance, it has long been known that aspirin (ASA) inhibits the activity of platelets in the coagulation system by suppressing their release of PF3. This, in turn, can lead to extended coagulation times for blood and plasma of patients taking aspirin. Nonetheless, as is well known, aspirin has been widely used as a pain killer and anti-inflammatory drug. Additionally, there has been a recent trend in medicine to prescribe a daily regimen of aspirin to reduce risk of heart attack. In fact, it has been estimated that over 20 million people in the U.S. presently take at least one aspirin a day for this reason. Further, recent suggestions have been made that sufferers of migraine headaches can benefit from a daily regimin of aspirin, and this could lead to over two million additional persons in the U.S. on daily aspirin therapy. This extensive and rapidly growing use of aspirin, which has heretofore somewhat recklessly proceeded without monitoring its effect on the patients' platelets, gives rise to an urgent need for sensitive tests which can be used to monitor aspirin therapy.

Another driving force for the development of good tests for platelet activity is the existence of platelet function abnormalities in patients. As an example, it has been discovered that full-term pregnancy pre-eclamptic women often have prolonged bleeding times. This has been attributed to low platelet counts, and also in some instances is thought to be due to abnormalities in platelets. See, J. Ramanathan et al., *Anesthesiol.*, 1989, 71, 188–91.

Additionally, in the area of quality control, a recent article points up the need for a sensitive test which can be used to differentiate platelet concentrates which retain functional integrity after storage from those which do not, and explains that there is presently no available method for accomplishing this. T. Hervig et al., *Clin. Chem.*, 1990, 36, No. 1, pp. 28–31.

Moreover, the presence of antiphospholipid antibodies has been associated with the occurrence of premature fetal death syndrome, see, for instance, D. A. Triplett, *College of American Pathologists Today*, July 1989, Vol. 3, No. 7 p. 61, thus giving rise to an additional group which would benefit from more sensitive and accurate tests for the presence of antiphospholipid antibodies. Further, to date there are no tests known to applicant for the quantitative determination of Platelet Factor 4 (PF4). However, as is known, PF4 neutralizes heparin, and thus an accurate determination of a patient's PF4 level should be an important and routine part of the application and monitoring of heparin therapy.

Another area to which this invention relates is hemostatic agents, which are are commonly used to control bleeding from wounds or from vessels during surgery. As an example, collagen preparations have been used as topical hemostatic agents. R. G. Mason et al., *Haemostasis*, 3, 31–45 (1974). Mason et al. report that the collagen preparations apparently accelerate formation of fibrin primarily by alteration of platelets rather than by direct action on the soluble components of the intrinsic coagulation system. In this regard, product literature for AVITENE, a microfibrillar collagen hemostat (MCH) available from Alcon Laboratories, Inc. of Fort Worth, Tex., also states that contacting the MCH with a bleeding surface attracts platelets which adhere to the fibrils and undergo the release phenomenon to trigger aggregation of platelets into thrombi in the interstices of the fibrous mass. Physician's Desk Reference (1987) pp. 588–589. In addition to topical hemostats, it is also known to use hemostatic pastes to stem bleeding from arteries during major surgery such as heart surgery. Despite these known hemostatic agents, there still exists a continuing need and desire for improved hemostatic agents. The applicant's invention also contemplates an improved hemostatic agent to address this need.

As is evident from the foregoing, there exists a continuing need for new, as well as more sensitive, accurate and reliable coagulation assays which can be used to determine coagulative properties of blood or plasma. There also exist needs for improvements in reagents for clotting tests, and in materials and methods for treating bleeding. The applicant's inventions address these needs.

SUMMARY OF THE INVENTIONS

A first preferred embodiment relates to a reagent for uniform activation of intrinsic coagulation which consists essentially of an aqueous solution of effective amounts of ellagic acid, phenol, and a suitable metal ion. The ellagic acid and metal ion are fully solubilized, and consistent activated plasma clotting times of less than about 40 seconds can be achieved for normal platelet-rich plasma.

A second preferred embodiment relates to a method for preparing a coagulation test reagent. This method comprises the steps of (a) preparing an aqueous solution by dissolving ellagic acid in water in the presence of a suitable base, (b) adding phenol to said aqueous solution, and (c) after said adding phenol, adding a suitable metal ion to said solution, said phenol being added in amounts sufficient to inhibit formation of insoluble metal hydroxides of said suitable metal ion, whereby the overall reagent is a solution.

A third preferred embodiment relates to the applicant's discovery that tannin or propyl gallate, in combination with a suitable metal ion, form an excellent activator of intrinsic coagulation. Accordingly, this embodiment involves a reagent for activation of intrinsic coagulation which contains a suitable metal ion and propyl gallate or tannin.

A fourth preferred embodiment relates to an aPTT reagent which comprises freeze-dried platelet substitute reconstituted with an aqueous solution containing (i) a suitable hydroxy-substituted aromatic compound and (ii) a suitable metal ion. This reagent gives consistent activated partial thromboplastin times of less than about 40 seconds for normal plasma, and, importantly, the overall reagent is a solution and has far superior sensitivity than prior aPTT reagents.

A fifth preferred embodiment relates to a coagulation test reagent kit. This kit comprises (i) a vial containing freeze-dried platelet substitute, and (ii) an aqueous solution comprising effective amounts of (i) a suitable hydroxy-substituted aromatic compound and (ii) a suitable metal ion. The hydroxy-substituted compound and suitable metal ion are fully solubilized. Further, the solution and platelet substitute, when combined in controlled amounts, form an overall reagent which is also a solution and which gives consistent aPTT values of less than about 40 seconds for normal plasma and has superior sensitivity.

A sixth preferred embodiment relates to an improvement in a reagent for activation of intrinsic coagulation which includes a suitable metal ion and a suitable hydroxy-substituted aromatic compound. In accordance with the invention, this reagent also includes dextran sulfate in effective amounts to increase sensitivity to heparin.

A seventh preferred embodiment relates to a platelet-sensitive method for assaying plasma for coagulation characteristics. This method includes the steps of (a) incubating at least one sample of the plasma in contact with a reagent containing effective amounts of a suitable hydroxy-substituted aromatic compound and a suitable metal ion, (b) after the incubating, adding calcium to the plasma sample to initiate clotting, and (c) after the adding calcium, measuring the time necessary for the sample to clot, the sample being at least essentially free from platelet substitute during clotting. In several preferred modes, this method provides assays for platelet activity, systemic lupus, PF4. platelet reserve, for signifying excessive circulating low-density lipoproteins, and platelet concentrate integrity. These assays were discovered following the applicant's surprising finding that reagents containing suitable hydroxy-substituted aromatic compounds and metal ions, heretofore known to activate Hagemann Factor, also cause the release of Platelet Factor 3 from platelets. This discovery is contrary to earlier reports in the field that ellagic acid does not alter platelet aggregation (platelet aggregation is generally considered a preliminary step to the release of PF3), A. Girolami et al., "Failure of Ellagic Acid to affect Platelet Aggregation in normal and Factor XII deficient Plasma," *Blut,* Band 31, Seite 107–112 (1975), or may even inhibit platelet aggregation. See J. Aznar et al., "Effect of Contact Factor (Factor XII+Factor XI) on Aggregation of Platelets," *Haemostasis* 3, 20–30 (1974).

An eighth preferred embodiment relates to a method for stemming bleeding, which comprises the step of (i) applying to a bleeding site an effective amount of a hemostatic agent including a suitable metal ion and a hydroxy-substituted aromatic compound.

The objects of the inventions are many. The inventions are intended to provide coagulation reagents and tests which are improved in sensitivity, uniformity of activation, and consistency in test results, and to provide sensitive and accurate assays for platelet activity and for conditions which affect measured platelet activity. Additional objects and advantages are apparent from the discussions both above and below.

DESCRIPTION OF THE PREFERRED EMBODIMENTS

For the purposes of promoting an understanding of the principles of the inventions, reference will now be made to certain preferred embodiments and specific language will be used to describe the same. It will nevertheless be understood that no limitation of the scope of the inventions is thereby intended, such alterations and further modifications, and such further applications of the principles of the inventions being contemplated as would normally occur to one skilled in the art to which the invention relates.

Improved Ellagic Acid Activator And Method For Preparation

As stated above, a first preferred embodiment relates to a reagent for uniform activation of intrinsic coagulation. This reagent consists essentially of an aqueous solution of ellagic acid, phenol, and suitable metal ion. The ellagic acid and suitable metal ion are fully solubilized, and consistent activated plasma clotting times of less than about 40 seconds can be achieved for normal platelet-rich plasma using the reagent.

As indicated, the reagent of this embodiment is a solution. Thus, the ellagic acid and suitable metal ion are fully solubilized, and the activity of the reagent, or at least a substantial percentage thereof, preferably about 85% or greater, and more preferably about 90–100%, is retained even after faltering through a 0.45 micron MILLIPORE filter. Accordingly, when herein a reagent is described as being a "solution", this means that a reagent's activity is substantially the same before and after filtering, such as through a 0.45 micron MILLIPORE filter. In this regard, it is preferred that the reagent, after such filtration. retain at least 85%, more preferably at least 90%, and most preferably levels approaching 100% of its original unfiltered activity. This retention of activity is evidenced by the similar respective clotting times for plasma obtained using the reagent before, and after Filtration, as is further illustrated in specific Example 34 below.

Further, and also importantly, the reagent gives consistent activated plasma clotting times (aPCT's) of less than about 40 seconds for normal platelet-rich plasma (the procedure for the activated plasma clotting time is discussed below). This consistency and time is achieved by including, along with the ellagic acid and phenol, an effective amount of suitable metal ion. The suitable metal ions are preferably, but not necessarily, divalent, with preferred divalent metal ions being transition metal ions such as $Cu^{2+}$, $Ni^{2+}$, and $Co^{2+}$, and most preferably $Ni^{2+}$. These suitable divalent metal ions are preferably provided by their water soluble halogen or sulfate salts, such as cupric sulfate, nickel chloride, or cobalt chloride. Additionally, a preferred monovalent metal ion is $Cu^+$, and a preferred trivalent metal ion is $Fe^{3+}$. $Ca^{2+}$ metal ions are less preferred, because calcium's presence in significant amount in the reagent, and thus during incubation of the sample, tends to prematurely initiate clotting mechanisms, thus interfering with obtaining accurate clotting times.

As to the amounts of the ellagic acid and the suitable metal ion, any amounts by which substantial activation of the intrinsic coagulation system can be achieved are acceptable. Preferably, the ellagic acid is included in molar concentrations of about $10^{-4}$ to $10^{-9}$, and more preferably about $10^{-4}$ to $10^{-5}M$. Additionally, it is preferred that the suitable metal ion be included in about an equal molar concentration to the ellagic acid, although concentrations greater than equal molar concentrations are also acceptable. Further, the more preferred activators of this embodiment include the phenol in an amount of about 0.02M.

A suitable buffer to maintain physiological pH is also preferably included. This buffer is preferably TRIS, although other suitable buffers, such as HEPES, can be used.

The excellent sensitivity and activating ability of these inventive ellagic acid-based activators is born out by the excellent results obtained for clotting tests reported further herein using these ellagic acid-based activators alone as the reagent, as well as by the superior aPTT reagents which are formed using these activators. Specific Examples 1–3 below further detail the preparation of intrinsic coagulation activators according to this embodiment.

A second preferred embodiment is a method for preparing a coagulation test reagent. The method comprises the steps of (a) preparing an aqueous solution by dissolving ellagic acid in water in the presence of a suitable base, (b) adding phenol to said aqueous solution, and (c) after Said adding phenol, adding a suitable metal ion to said solution, said phenol being added in mounts sufficient to inhibit formation of insoluble metal hydroxides of said metal ion, whereby the overall reagent is a solution. Many suitable bases which aid in the aqueous dissolution of ellagic acid are known, and accordingly could be used within the scope of this invention. However, the applicant's preferred base for this purpose is tetramethylammonium hydroxide. It is important that the ingredients be added in the order provided by this method, as any other order leads to inferior reagents containing insoluble materials which interfere with uniformity of activation and consistency of result. Additional aspects of this embodiment, including those relating to the preferred amounts of ellagic acid and amounts and types of metal ions, are analogous to those detailed in the first embodiment discussed above and can also be found in Examples 1–3 below.

Propyl Gallate and Tannin Coagulation Activators

As stated above, a third preferred embodiment relates to the applicant's discovery that tannin and propyl gallate, in combination with a suitable metal ion, each provide a uniform, consistent activator of intrinsic coagulation. Accordingly, this third embodiment relates to a reagent for activating intrinsic coagulation; which reagent contains a suitable metal ion and propyl gallate or tannin.

Although reagents in accordance with this embodiment need not be solutions to be effective, it is preferred that they be solutions in order to achieve the same significant advantages discussed in connection with the embodiments set forth above. Propyl gallate and tannin provide advantage over ellagic acid and similar suitable hydroxy-substituted aromatic compounds, because they more readily dissolve and remain so dissolved in aqueous solutions.

The reagent of this embodiment also contains a suitable metal ion. The metal ions need not be, but preferably are, divalent metal ions, with preferred suitable divalent metal ions being transition metal ions such as $Ni^{2+}$, $Cu^{2+}$ and $Co^{2+}$, most preferably $Ni^{2+}$. As in the first embodiment, a preferred monovalent metal ion is $Cu^{+}$, and a preferred trivalent ion is $Fe^{3+}$. The tannin and propyl gallate, and the metal ion, can be included in the reagent in any amounts by which the reagent activates coagulation. Preferably, however, propyl gallate is included in the reagent in molar concentrations of about $10^{-9}$ to $10^{-2}$, and more preferably $10^{-2}$ to $10^{-3}M$, and tannin is preferably included in the reagent in amounts of about $10^{-5}$ to about $10^{-1}$ weight %, and more preferably about 0.005 weight %. The metal ions are preferably included in mounts of about $10^{-9}$ to $10^{-4}M$, and more preferably about $10^{-4}$ to $10^{-5}M$. Additionally, the preferred divalent metal ions are preferably provided by their water soluble halogen of sulfate salts, such as cupric sulfate, nickel chloride, or cobalt chloride.

In addition to the above ingredients, the reagent of this embodiment also preferably includes a suitable buffer to maintain physiological pH. Many acceptable buffers of this type are known, including for instance 4-(2-hydroxyethyl)-1-piperazineethanesulfonic acid (also known as HEPES) and Tris(hydroxymethyl)aminomethane (also known as TRIS). The applicant's preferred buffer, however, is TRIS, which is most preferably included in a concentration of about 0.01M.

Also, in one preferred mode, the reagent of this embodiment includes platelet substitute, and accordingly is an activated partial thromboplastin time reagent. The preferred platelet substitute is ASOLECTIN, which is a soy bean-derived phospholipid available from Associate Concentrates, Inc. of Woodside N.Y., although many other suitable platelet substitutes are available, including for instance cephalin derived from rabbit or other animal brain. Additional details regarding the preparation of reagents of this embodiment are provided in Examples 7–9, 13–15, 19–21 and 28–30 below.

Highly Sensitive aPTT Reagents and Kits

As discussed above, prior aPTT reagents have been criticized for their lack of sensitivity. The applicant has developed aPTT reagents having far superior sensitivity than prior reagents, and accordingly a fourth preferred embodiment provides a reagent for activation of intrinsic coagulation which comprises freeze-dried platelet substitute reconstituted with an aqueous solution containing effective activating amounts of (i) a suitable hydroxy-substituted aromatic compound, and (ii) a suitable metal ion. This overall inventive reagent is a solution, and gives consistent aPTT values of less than about 40 seconds for normal platelet poor plasma. Moreover, this reagent is highly sensitive, which is demonstrated by the reagent giving aPTT values of at least about 200 seconds for 1 u/ml heparinized normal platelet poor plasma. It is preferred that the aqueous solution be an activator as described in the first and third embodiments above. Further, the solution form of the overall reagent can be demonstrated by the similar aPTT values obtained before and after filtration, as is illustrated in Example 35 below.

To exemplify reagents according to this embodiment, aPTT tests were performed on normal human plasma using aPTT reagent which was prepared by reconstituting 0.001 g freeze-dried platelet substitute (ASOLECTIN) with 5 ml of the intrinsic coagulation activators ("Intrinsic Activators") from the Examples indicated in Table 1 below. The aPTT tests were run in the usual manner by adding 0.1 ml of the prepared aPTT reagent to a 0.1 ml sample of citrated platelet-poor normal plasma. The plasma was then incubated at 37° C. for 5 minutes, whereafter calcium chloride was added to the sample initiate clotting, and the time necessary for the samples to clot was measured. The results of these tests are set forth in Table 1.

TABLE 1

| Intrinsic Activator | aPTT (sec.) |
| --- | --- |
| Copper/ellagic acid (Ex. 1) | 24.4 |
| Nickel/ellagic acid (Ex. 2) | 27.5 |
| Cobalt/ellagic acid (Ex. 3) | 20.3 |
| Copper/propyl gallate (Ex. 7) | 29.0 |
| Nickel/propyl gallate (Ex. 8) | 29.4 |
| Cobalt/propel gallate (Ex. 9) | 30.3 |
| Copper/tannin (Ex. 13) | 30.7 |

TABLE 1-continued

| Intrinsic Activator | aPTT (sec.) |
|---|---|
| Nickel/tannin (Ex. 14) | 29.1 |
| Cobalt/tannin (Ex. 15) | 28.0 |

In another set of experiments, the sensitivity of the inventive aPTT reagents was compared to that of known commercial reagents. For instance, heparin sensitivity of a preferred aPTT reagent according to the invention and various commercial aPTT reagents was compared. Accordingly, 0.001 g of lyophilized ASOLECTIN platelet substitute ("PS") was reconstituted with 5 ml of the applicant's preferred Intrinsic Activator prepared in Example 2 (this aPTT reagent is indicated by "PS/5 ml" in Table 2). Also, 0.001 g of lyophilized ASOLECTIN was reconstituted with only 2 ml of this Intrinsic Activator (indicated as "PS/2 ml" in Table 2). These inventive aPTT reagents, and the commercial aPTT reagents identified in Table 2 below, were used to perform aPTT tests on normal human plasma and on heparinized (1 u/ml) normal human plasma. The results demonstrate that the inventive aPTT reagents have highly superior sensitivity to heparin, and gave aPTT values in excess of 200 seconds for 1 u/ml heparinized plasma, even ranging above 250 seconds. This superior sensitivity to heparin represents a significant increase over known aPTT reagents.

TABLE 2

| aPTT Reagent | Normal Control | Heparinized |
|---|---|---|
| PS/5 ml | 30 sec. | 345 sec. |
| PS/2 ml | 28 sec. | 245 sec. |
| Dade ACTIN | 28 sec. | 125 sec. |
| Ortho ACTIVATED THROMBOFAX | 22 sec. | 100 sec. |

In general, a reagent which has superior sensitivity to heparin will also have superior sensitivity to Factor deficiencies. In another set of experiments, this proved to be true for the inventive reagents. Plasma samples having Factor VIII, IX, and X deficiencies were assayed using an inventive aPTT reagent and commercial aPTT reagents. The inventive aPTT reagent was prepared by reconstituting 0.001 g of lyophilized ASOLECTIN platelet substitute "PS" with 10 ml of the Intrinsic Activator of Example 2 (this aPTT reagent is indicated as "PS/10 ml" in Table 3). The results of the respective aPTT tests are given in Table 3 below. As is shown, the inventive aPTT reagents gave aPTT values in excess of 150 seconds for the Factor deficient plasmas, even ranging above 200 seconds. These values represent a marked improvement over known aPTT reagents.

TABLE 3

| Reagent | aPTT for Factor VIII deficiency | aPTT for Factor IX deficiency | aPTT for Factor X deficiency |
|---|---|---|---|
| PS/10 ml | 212.5 | 249.0 | 203.2 |
| Dade ACTIN | 50.1 | 94.9 | 94.4 |
| Ortho ACTIVATED THROMBOFAX | 48.4 | 53.2 | 40.7 |

A fifth preferred embodiment relates to a coagulation test reagent kit from which the preferred coagulation activators of the fourth embodiment above can be conveniently and effectively prepared. This kit comprises (i) a vial containing freeze-dried platelet substitute, and (ii) an aqueous solution comprising effective amounts of (i) a suitable hydroxy-substituted aromatic compound and (ii) a suitable metal ion. The hydroxy-substituted aromatic compound and the metal ion are fully solubilized. Further, the aqueous solution and platelet substitute, when combined in controlled amounts, form a reagent which is also a solution and which gives consistent aPTT values of less than about 40 seconds for normal plasma, and which gives aPTT values of at least about 200 seconds for 1 u/ml heparinized normal platelet poor plasma. Preferably, the platelet substitute is included in the vial in an amount whereby reconstitution with about 2 ml to about 10 ml of the solution forms a reagent giving the indicated aPTT values. Further preferred aspects of this embodiment correspond to those of the fourth embodiment discussed above.

The applicant has also discovered that the preferred aPTT reagents and kits according to the fourth and fifth embodiments above can be used in sensitive assays to detect lupus anticoagulant. Thus, these reagents and kits form the basis for a method for detecting the presence of lupus anticoagulant in subject plasma, which comprises the steps of (a) incubating platelet poor subject plasma in contact with a reagent according to the fourth embodiment above, (b) adding calcium to the platelet poor subject plasma in effective amounts to initiate clotting, and (c) measuring the time necessary for the platelet poor subject plasma to clot. Typically, aPTT times at least about 5 seconds greater than those obtained for normal controls can signify the presence of lupus anticoagulant. In the applicant's work, using this inventive method, lupus anticoagulant plasmas have typically exhibited aPTT times in excess of 50 seconds, and often in excess of 100 seconds or more.

Heparin Sensitive Reagents With Dextran Sulfate

As stated above, a sixth preferred embodiment relates to an improvement in a reagent for activation of intrinsic coagulation. In accordance with this embodiment, a coagulation activating reagent containing a suitable metal ion and a suitable hydroxy-substituted aromatic compound, also contains dextran sulfate in effective mounts to increase sensitivity of the reagent to heparin.

Although not required, it is preferred that the reagents according to this embodiment be solutions, as this term is defined above. Further, although other suitable hydroxy-substituted compounds can be used, reagents according to this embodiment preferably contain ellagic acid, propyl gallate or tannin. The respective preferred amounts of these three compounds in the reagents of this embodiment correspond to their preferred amounts in the reagents of embodiments described above. Similarly, the suitable metal ions are preferably divalent, with preferred suitable divalent metal ions being transition metal ions such as $Ni^{2+}$, $Cu^{2+}$ and $Co^{2+}$, preferably included in the same amounts as in the embodiments discussed above.

Additionally, the reagents of this embodiment, in one preferred mode, also contain platelet substitute, and thus form heparin sensitive aPTT reagents. Again, the preferred platelet substitute is ASOLECTIN, and it is preferred that the overall reagent including the platelet substitute be a solution.

The dextran sulfate is preferably present in an amount between about 0.008 and 0.012 weight mg %, more preferably about 0.01 weight mg %, although any amount which increases sensitivity to heparin is sufficient. It is believed that dextran sulfate neutralizes available PF4, thus leading to increased heparin sensitivity. Thus, other substances, such as protamine sulfate, which are equivalents to dextran sulfate and have substantially the same properties, are contemplated as being within the scope of the invention.

To verify significant increase in heparin sensitivity, heparinized plasma samples (1 u/ml) were tested for aPTT and aPCT using reagents with ("w/") and without ("w/o") dextran sulfate ("DS"). The results are set forth in Table 4 below. The composition and preparation of the preferred reagents used is given in the specific Examples which are indicated in parentheses in Table 4. The "aPTT w/o DS" reagent indicated in Table 4 was prepared indentically to the reagent of Example 26, except without the addition of the dextran sulfate. The results demonstrate that the addition of dextran sulfate substantially increases sensitivity to heparin.

TABLE 4

| Plasma | aPCT w/DS (Ex. 5) | aPCT w/o DS (Ex. 2) | aPTT w/DS (Ex. 26) | aPTT w/o DS |
|---|---|---|---|---|
| Heparinized | 194.8 | 137.9 | 129.6 | 87.5 |
| Normal Control | 29.4 | 29.0 | 27.7 | 27.7 |

Platelet-Sensitive Assays

A seventh preferred embodiment relates to a platelet-sensitive method for assaying plasma. This method includes the steps of (a) incubating the plasma in contact with a reagent containing effective amounts of a suitable hydroxy-substituted aromatic compound and a suitable metal ion to cause the platelets to release Platelet Factor 3, (b) after the incubating, adding calcium to the plasma to initiate clotting, and (c) after the adding calcium, measuring the time necessary for the plasma to clot, the plasma being essentially free from platelet substitute during clotting.

As the applicant has discovered, suitable hydroxy-substituted aromatic compounds and metal ions, which were heretofore known to activate Hagemann factor, also cause platelets to release Platelet Factor 3. Accordingly, the method of this embodiment provides assays which are highly sensitive to platelets.

It is preferred that the reagent used in the incubating step be a solution as defined above. Further, the hydroxy-substituted aromatic compound included in the reagent can be any suitable one as known in the art. Preferred, however, are ellagic acid, propyl gallate and tannin, or suitable derivatives thereof, with ellagic acid being most preferred. These compounds are preferably included in the reagent in amounts corresponding to those disclosed above for other embodiments. Likewise, the metal ion, which is preferably a divalent transition metal ion (preferred again are $Ni^{2+}$, $Cu^{2+}$ and $Co^{2+}$, most preferably $Ni^{2+}$), is included in the same concentrations as discussed above for other embodiments. Of course, in order for the assay to be sensitive to platelets, the plasma being assayed must be at least essentially free from, and preferably free from platelet substitute during clotting. Accordingly, the preferred reagents used in this embodiment are at least essentially free from, and more preferably free from platelet substitute. As indicated above, in several preferred modes, this platelet-sensitive method provides assays for platelet activity, systemic lupus, PF4, platelet reserve, which can signify excessive circulating low-density lipoproteins, and for platelet integrity. Each of these is discussed below and each provides an important assay to meet needs in this field which prior tests have not.

I. Activated Plasma Clotting Time (aPCT) Test

In this test, the platelet-sensitive method discussed above is performed on platelet-rich plasma. Accordingly, this test provides a sensitive and accurate measure of platelet activity of plasma. This test has been termed the "activated plasma clotting time" (aPCT) test by applicant.

APCT tests were performed on normal platelet-rich human plasma using preferred Intrinsic Activators of the invention as the aPCT reagents. Accordingly, a 0.1 ml amount of the Intrinsic. Activator of the Example indicated in Table 5 below was added to a 0.1 m sample of normal citrated platelet-rich plasma. The plasma was then incubated for 5 minutes, whereafter calcium chloride was added to the plasma to initiate clotting. The time necessary for the samples to clot was measured, and the results are given in Table 5 below.

TABLE 5

| Intrinsic Activator | aPCT (sec.) |
|---|---|
| Copper/ellagic acid (Ex. 1) | 30.3 |
| Nickel/ellagic acid (Ex. 2) | 30.0 |
| Cobalt/ellagic acid (Ex. 3) | 26.5 |
| Copper/propyl gallate (Ex. 7) | 30.4 |
| Nickel/propyl gallate (Ex. 8) | 31.0 |
| Cobalt/propyl gallate (Ex. 9) | 29.4 |
| Copper/tannin (Ex. 13) | 32.4 |
| Nickel/tannin (Ex. 14) | 30.9 |
| Cobalt/tannin (Ex. 15) | 32.9 |

II. Determination of Platelet Reserve

In a normal subject, there is an excess of platelets beyond the quantity and quality required to support normal coagulation, which is herein referred to as the "platelet reserve". The applicant has discovered that the aPCT test can be used to accurately and reliably assay for platelet reserve. Accordingly, another preferred mode of this embodiment is an assay for determining platelet reserve in subject plasma. In this assay, the activated plasma clotting times of serial dilutions of platelet rich subject plasma with platelet poor subject plasma are determined. By analysis of the aPCT values obtained for the dilutions, a value representative of the platelet reserve can be determined.

For example, the platelet reserve can be determined by preparing dilutions of a patient's platelet rich plasma (PRP) with the patient's platelet poor plasma (PPP), and performing aPCT tests on the dilutions. Typically, the following dilutions can be used (PRP/PPP): 100% PRP; 50% PRP/50% PPP; 25% PRP/75% PPP; and 12.5% PRP/87.5% PPP. The aPCT times are then plotted on a graph having % PRP on one coordinate and aPCT values on the other. An aPTT test is performed on PPP, and the time obtained used as a baseline on the graph. Additionally, the aPCT value obtained using 100% platelet-rich plasma can be used as a baseline, although using this value as a baseline may in some instances lead to innaccurate results, such as where the patient has abnormally functioning platelets.

The applicant has found that the dilution curve will most often have linearity extending from 12.5% to 50% PRP, and almost always from 25% to 12.5% PRP. Thus, preferably a line is drawn through the aPCT values for the 25% and 12.5% PRP dilutions. This line is extended until it intersects the baseline. The % PRP corresponding to the point of intersection with the baseline is then subtracted from 100% to obtain the patient's platelet reserve.

Figure 1:
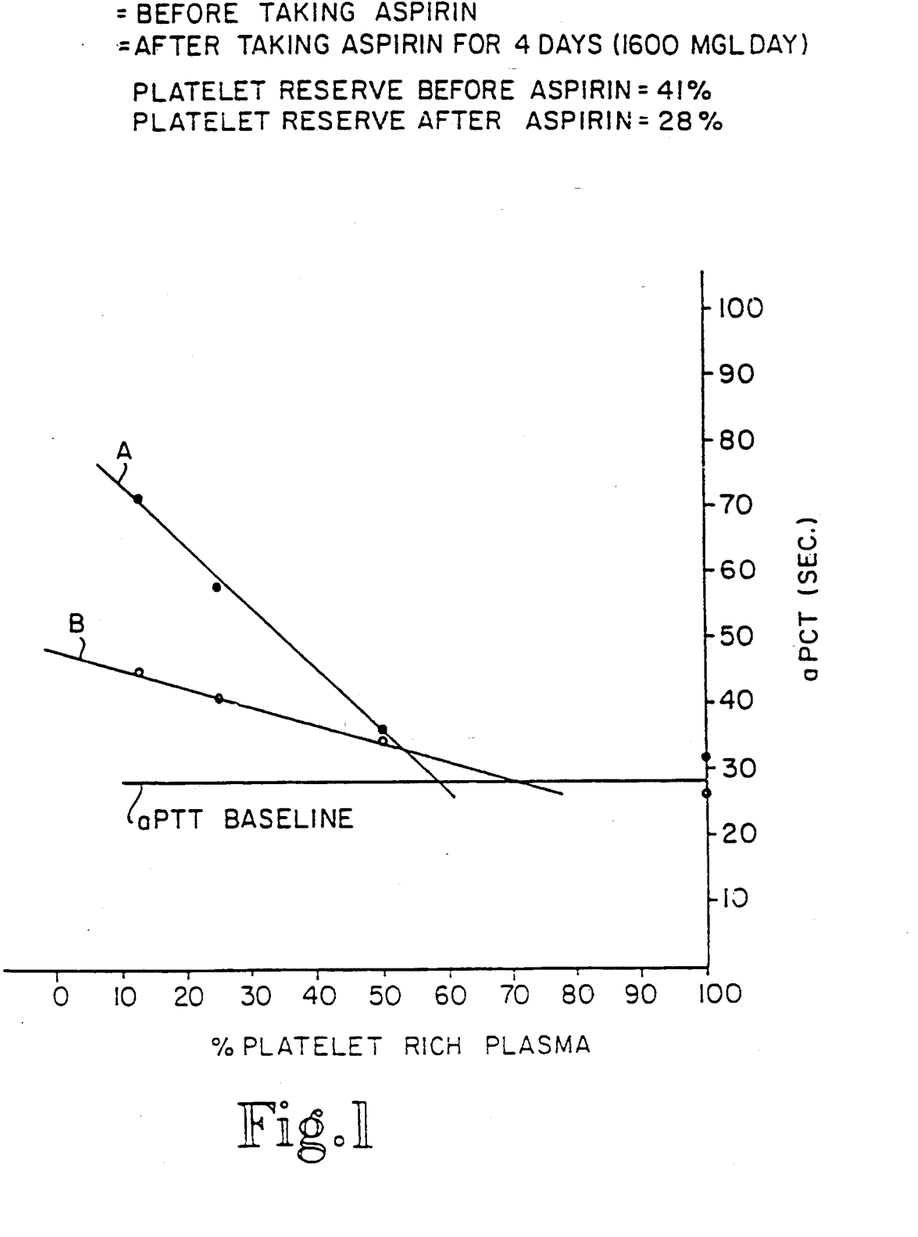
FIG. 1 shows a platelet reserve determination for a normal patient before and after aspirin therapy.
Figure 2:
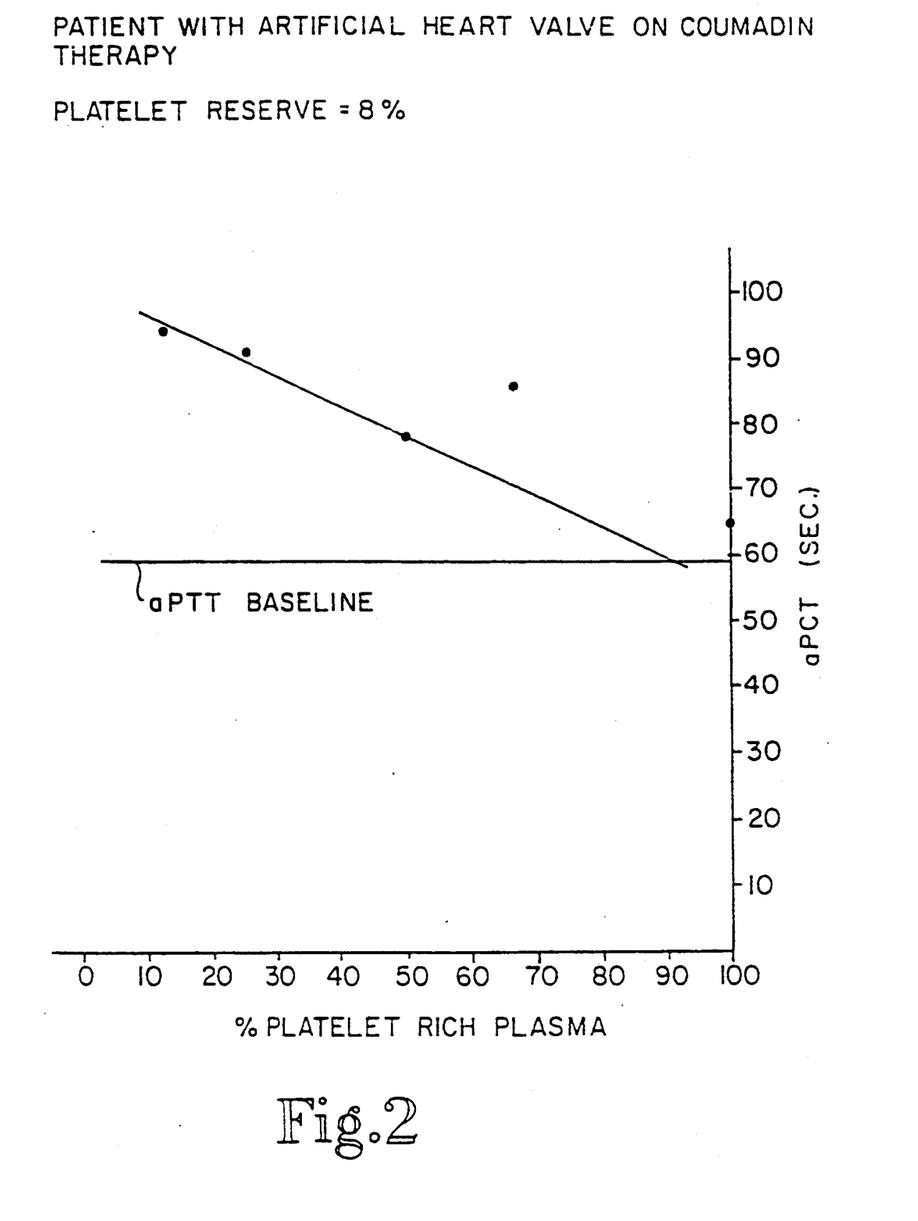
FIG. 2 shows a platelet reserve determination for a patient on coumadin therapy.
Figure 3:
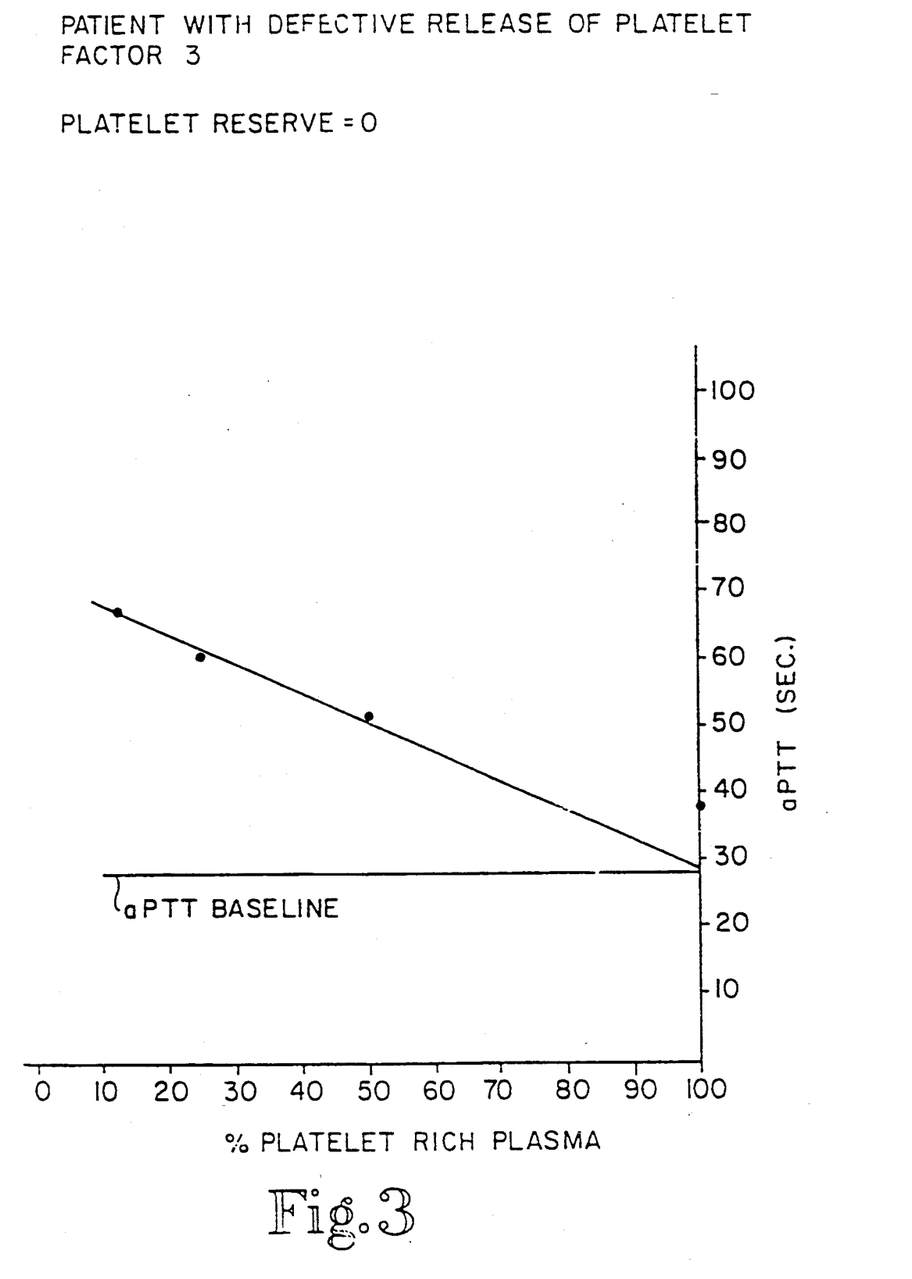
FIG. 3 shows a platelet reserve determination for a patient with defective Platelet Factor 3 release.

FIGS. 1-3 demonstrate platelet reserve determinations performed in accordance with this preferred embodiment. FIG. 1 shows a normal patient having a platelet reserve of 41% prior to aspirin therapy (line "A"). After four days of aspirin therapy at 1600 milligrams/day, the patient's platelet reserve was again determined, resulting in line "B". As can be seen, the patient's platelet reserve after the aspirin therapy decreased to 28%. FIG. 1 thus demonstrates that the platelet reserve is an excellent and sensitive test for monitoring aspirin therapy or other therapies which effect the activity of platelets. The above platelet reserve figures were calculated using an aPTT baseline. Using the aPCT value for 100% PRP as a baseline, a value of about 44% for platelet reserve prior to aspirin therapy is obtained, which is a good estimate of platelet reserve and does not require the additional step of performing an aPTT test.

FIG. 2 shows a platelet reserve determination on a patient on coumadin therapy. The patient's platelet reserve was 8%, well below the normal of about 30% to 40%. Thus, it was demonstrated that the platelet reserve test can also be performed on patients on coumadin or like therapy.

FIG. 3 shows a platelet reserve determination on a patient with defective Platelet Factor 3 release. As is shown, the patient's platelet reserve was determined to be 0%. Accordingly, the platelet reserve can also be used to detect functional defects of platelets.

Figure 4:
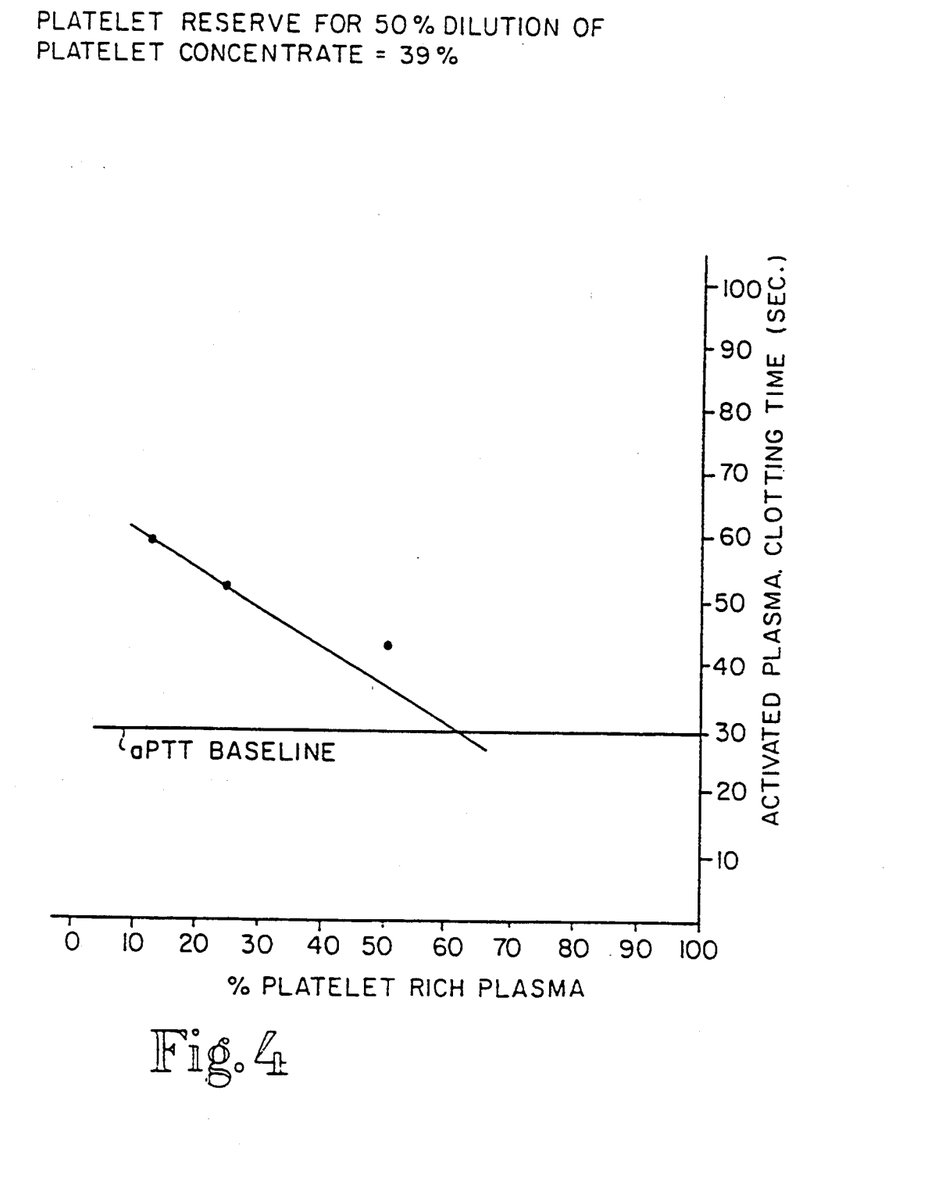
FIG. 4 shows a platelet reserve determination on a platelet concentrate.

In another experiment, it was demonstrated that a platelet reserve determination could be used to assay the functional integrity of platelets in a platelet concentrate. Accordingly, a platelet concentrate was obtained from Universal Reagents of Indianapolis, Ind. The concentrate had a platelet count of 2,080,000/ml. This concentrate was diluted 50% with platelet poor plasma. This 50% diluted concentrate was then subjected to a platelet reserve assay as was performed for FIGS. 1-3. The results are shown in FIG. 4, and demonstrate that the 50% dilution had a platelet reserve of 39%. Accordingly, taking into account the 50% dilution factor, the platelet concentrate was determined to have a platelet reserve of 78% (39%×2). It will be understood that alternative analyses can be used to determine platelet reserve from the respective aPCT values obtained for the dilutions, and that graphical representation is unnecessary.

III. Detection of Lupus Anticoagulant

It has been discovered that the platelet-sensitive method provides a sensitive and specific assay for lupus anticoagulant when performed on platelet-poor plasma. For example, Table 6 summarizes studies which demonstrate this specificity and sensitivity. Table 6 shows the clotting times obtained for various abnormal plasmas, including lupus plasmas (platelet poor), using the intrinsic activator of Example 2 (Ni/ellagic acid) as the reagent, as compared to aPTT values obtained for these same plasmas (using an aPTT reagent prepared as in Example 26 except without the addition of dextran sulfate). The variety of plasma's were obtained from Universal Reagents of Indianapolis, Ind. As is demonstrated, the lupus test of this preferred mode has outstanding specificity and sensitivity for and to lupus anticoagulant.

TABLE 6

| Type of Plasma | aPTT | aPCT |
|---|---|---|
| platelet rich plasma | 25.8 | 26.0 |
| platelet poor plasma | 26.2 | 71.2 |
| Lupus anticoagulant | 39.0 | 263.1 |
| Lupus anticoagulant | 48.7 | 269.5 |
| ANA speckled | 39.7 | 67.4 |
| ANA speckled | 32.2 | 62.9 |
| ANA homogenous | 33.8 | 65.3 |
| ANA homogenous | 32.2 | 54.6 |
| nDNA Antibody | 33.9 | 75.7 |
| SCL-70 | 34.3 | 46.8 |
| RNP | 44.7 | 71.2 |
| SSA Antibody | 19.9 | 37.0 |
| SSB Antibody | 37.7 | 61.5 |

Table 7 below compares the lupus anticoagulant sensitivity of the applicant's preferred lupus test (using the Intrinsic Activator of Example 2 as the reagent), to the sensitivity obtained using various commercial aPTT reagents. The plasmas tested were all platelet poor. As shown, the preferred lupus test of this mode is far superior than commercial aPTT reagents and tests in the detection of lupus anticoagulant.

TABLE 7

| Type of Plasma | Ex. 2 | Ortho aPTT | Dade ACTIN | Biodata |
|---|---|---|---|---|
| Lupus anticoagulant | 174.4 | 31.6 | 44.7 | 51.1 |
| Lupus anticoagulant | 221.9 | 32.6 | 46.1 | 61.0 |
| Norm. Human Plasma (platelet poor) | 64.8 | 25.3 | 27.9 | 32.8 |

IV. Assay For Lipoprotein Defect

It has been demonstrated that the applicant's preferred platelet-sensitive method can be used to signify possible Type II lipoprotein defects. Subjects having this condition have excessively high circulating low-density lipoproteins. In this assay, the platelet-sensitive method is performed on platelet-poor subject plasma and on platelet-rich subject plasma (this latter test is simply an aPCT test). The two measured clotting times are then compared, whereby the lack of a significant difference can signify excessive circulating low-density lipoprotein.

For example, such an assay was performed on a patient suspected of having a Type II lipoprotein defect. The patient's platelet rich plasma exhibited an aPCT in accordance with the invention of 31.2 seconds (using the intrinsic activator of Example 2 as the aPCT reagent). The patient's platelet poor plasma demonstrated a clotting time of 33.1 seconds using the same reagent, as opposed to normal values of about 60 seconds or more for normal platelet poor plasma. A possible Type II lipoprotein defect was thus signified, which was confirmed by lipoprotein electrophoresis of the patient's plasma.

V. Assay For Platelet Factor 4

The platelet-sensitive method can also be used to test for Platelet Factor 4 release in plasma. In the PF4 assay, the platelet-sensitive method is performed on plasmas having varying ratios of platelets to heparin units, whereby neutralization of the heparin present by Platelet Factor 4 released by the platelets can be observed.

Of course, the varying ratios can be obtained by adjusting the level of platelets, or the level of heparin, or by adjusting the level of both.

For example, in one method, platelet rich subject plasma and at least one dilution of platelet rich subject plasma (with platelet poor plasma) are equally heparinized. The measured clotting times are then compared, whereby a significantly lower clotting time for the heparinized platelet rich plasma as compared to the dilution can indicate release of sufficient Platelet Factor 4 in the platelet rich plasma to neutralize the heparin. In an experiment using this approach, two plasma samples, each containing 1 unit of heparin per ml, were prepared. The first sample was 100% platelet rich plasma, and the second was 50% platelet rich plasma and 50% platelet poor plasma. The clotting times obtained using the intrinsic activator of Example 2 as a reagent were 31.3 seconds for the 100% PRP, and 208.6 seconds for the 50% dilution. The relatively short clotting time for the 100% PRP indicates the release of sufficient PF4 to neutralize the heparin. The relatively long clotting time for the 50% dilution indicates that less PF4 has been released (due to the reduced concentration of platelets) so that less heparin was neutralized, leading to the longer clotting time. The ability of the plasma used in the two samples to release PF4 was thus demonstrated. Had the plasma had a defect in PF4 release or function, the aPCT value for the 100% PRP would have been significantly longer.

Figure 5:
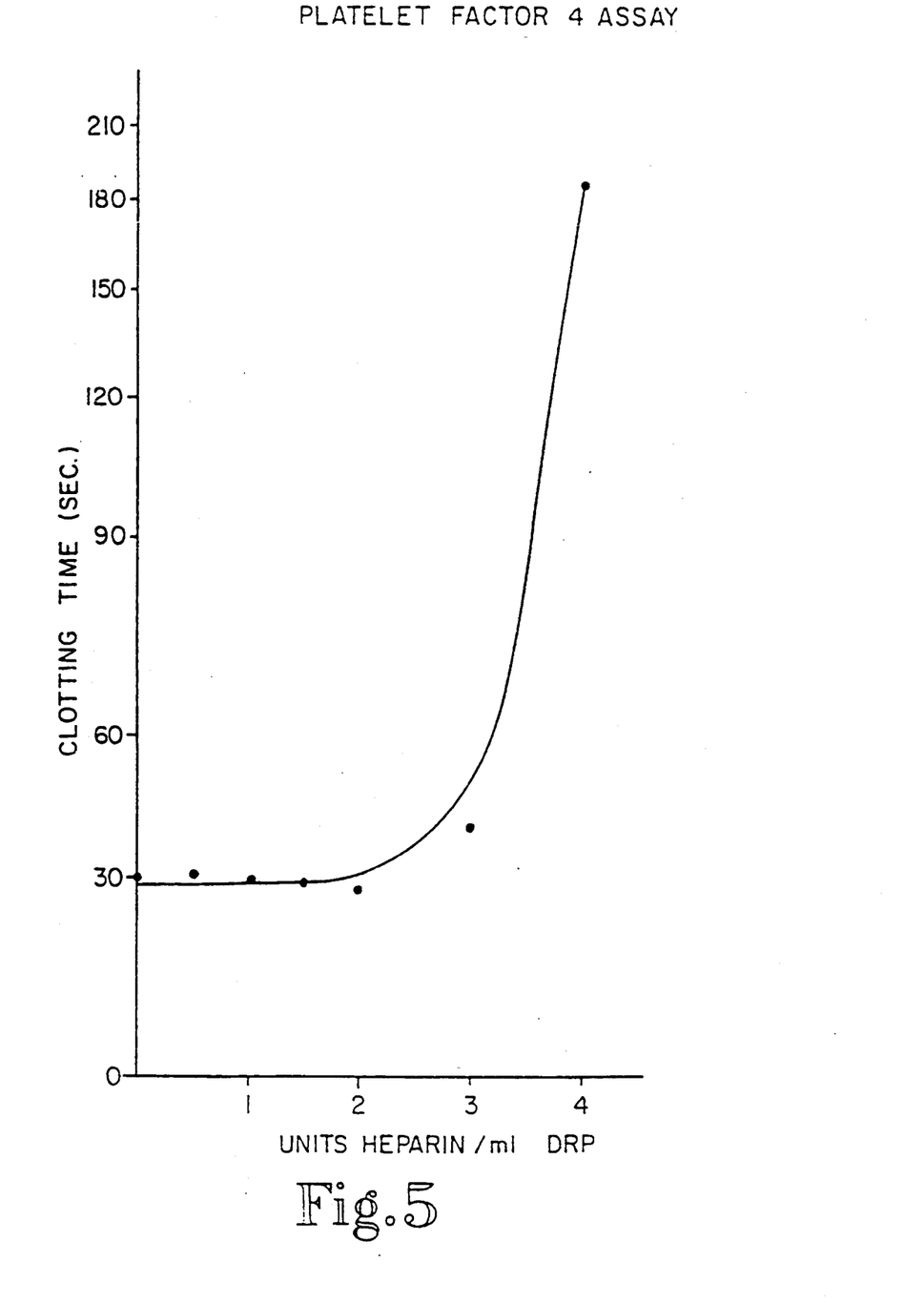
FIG. 5 shows a clotting time determination of plasma samples with various platelet to heparin ratios.

It will be appreciated that significantly more precise measures of the levels of PF4 in plasma samples can be obtained by assaying plasmas having several ratios of platelets to heparin to determine more precisely the point of neutralization of the heparin by PF4. Accordingly, in another experiment, dilutions were prepared having effectively the levels of heparin per ml of PRP indicated in Table 8 below. The clotting times were obtained for each of these dilutions using the intrinsic activator of Example 2 as the reagent. The results are tabulated in Table 8, and graphically represented in FIG. 5. These results demonstrate the sufficient release of PF4 in the patient's platelet-rich plasma to neutralize between 3 and 4 units of heparin per ml. Thus the inventive PF4 assay provides a way to accurately determine PF4 levels in plasma samples.

TABLE 8

| U/Heparin/ml | Clotting Time (sec) |
|---|---|
| 0 | 30.1 |
| 0.5 | 30.1 |
| 1.0 | 29.6 |
| 1.5 | 28.8 |
| 2.0 | 27.3 |
| 3.0 | 39.4 |
| 4.0 | 186.8 |

Activated Whole Blood Clotting Time

The applicant has also demonstrated that the preferred intrinsic activators can be used in performing activated whole blood clotting time tests (A.W.B.C.T). Accordingly, the activated whole blood clotting time of fresh human blood was determined by incubating 0.1 ml fresh human blood and 0.1 ml of the intrinsic activator of Example 2 in a Fibrometer for 5 minutes. 0.1 ml 0.02M $CaCl_2$ was added, whereafter the A.W.B.C.T. value obtained was 43.4 seconds. Similar tests on two additional fresh whole blood samples gave A.W.B.C.T. values of 38.4 and 38.9 seconds. Thus the inventive Intrinsic Activators are useful for whole blood as well as plasma-based tests.

Method and Materials to Stem Bleeding

In yet another set of experiments, the applicant has discovered that bleeding from wounds can be stopped up to six time faster by applying to the bleeding site an effective amount of a hemostatic agent including a suitable metal ion and a hydroxy-substituted aromatic compound. Preferred are reagents according to the first embodiment above, which can in this embodiment also optionally include a platelet substitute, preferably ASOLECTIN, and also preferred are reagents according to the third embodiment above.

For example, in one experiment the intrinsic activator of Example 2 was applied to a portion of fibrous material (e.g. filter paper) and this material was then applied to a bleeding finger wound. The wound stopped bleeding in about 16 seconds. Another bleeding finger wound treated similarly with an unmodified portion of the fibrous material stopped bleeding only after 94 seconds. It was thus demonstrated that the method of this embodiment provides an outstanding way to stem bleeding.

It will be understood that there are other materials to which the reagents can be applied in particular bleeding applications. For instance, it is known to prepare pastes by reconstituting cryoprecipitates of human blood with thromboplastin for application to bleeding sites during surgery such as coronary surgery. In one preferred mode of this embodiment, the indicated reagents are used in the reconstitution of the cryoprecipitates in the preparation of such pastes. The resulting pastes have superior ability to slow or stop bleeding, and thus these materials themselves constitute a further inventive embodiment.

The following Examples are given in order to further illustrate the invention.

EXAMPLE 1

ELLAGIC ACID AND COPPER II INTRINSIC ACTIVATOR 0.18 g tetramethylammonium hydroxide were dissolved in 1,000 ml water. 0.034 g ellagic acid were then dissolved in this tetramethylammonium hydroxide solution. 1.5 g phenol were then dissolved in the tetramethylammonium hydroxide-ellagic acid solution, whereafter 1.0 ml 0.1M cupric sulfate were added and the resulting solution mixed for 10 minutes with teflon coated stirring bar on a stir-plate. 1.2 g TRIS buffer were then dissolved into the solution. The resulting solution was clear and free from any visible particulate or other suspended matter.

EXAMPLE 2

ELLAGIC ACID AND NICKEL INTRINSIC ACTIVATOR

Example 1 was repeated except 1.0 ml 0.1M nickel chloride was used instead of the 1.0 ml 0.1M cupric sulfate to form an ellagic acid/nickel coagulation activator which was also a clear solution free from visible particulate or other suspended matter.

EXAMPLE 3

ELLAGIC ACID AND COBALT INTRINSIC ACTIVATOR

Example 1 was repeated except 1.0 ml 0.1M cobalt chloride was used instead of the 1.0 ml 0.1M cupric sulfate, and the TRIS buffer was not added. A clear ellagic acid/cobalt coagulation activator solution was formed. This unbuffered activator performs similarly to the buffered activators in Examples 1 and 2. The buffer further stabilizes the activators over time.

EXAMPLE 4

HEPARIN SENSITIVE INTRINSIC ACTIVATOR WITH ELLAGIC ACID, DEXTRAN SULFATE, AND COPPER II

Example 1 was repeated except 1.0 ml 100 mg/dl dextran sulfate was added along with the cupric sulfate to form a coagulation activator sensitive to heparin

EXAMPLE 5

HEPARIN SENSITIVE INTRINSIC ACTIVATOR WITH ELLAGIC ACID, DEXTRAN SULFATE, AND NICKEL

Example 2 was repeated except 1.0 ml 100 mg/dl dextran sulfate was added along with the nickel chloride. A heparin sensitive coagulation activator with ellagic acid, dextran sulfate, and nickel was thus formed.

EXAMPLE 6

HEPARIN SENSITIVE INTRINSIC ACTIVATOR WITH ELLAGIC ACID, DEXTRAN SULFATE AND COBALT

Example 3 was repeated except 1.0 ml 100 mg/dl dextran sulfate was added along with the cobalt chloride to form a heparin sensitive coagulation activator with ellagic acid and cobalt.

EXAMPLE 7

PROPYL GALLATE AND COPPER II INTRINSIC ACTIVATOR 0.5 g propyl gallate were dissolved in 1,000 ml water. 1.0 ml 0.1M cupric sulfate were then added, whereafter the solution was mixed for 10 minutes with teflon-coated stir bar. 1.2 g TRIS buffer were then dissolved in this solution, which was thereafter stirred for an additional 10 minutes. A propyl gallate/copper coagulation activator was formed as a clear solution without any visible suspended materials.

EXAMPLE 8

PROPYL GALLATE AND NICKEL INTRINSIC ACTIVATOR

Example 7 was repeated except 1.0 ml 0.1M nickel chloride was used instead of the cupric sulfate. A clear solution-form coagulation activator with propyl gallate and nickel was formed.

EXAMPLE 9

PROPYL GALLATE AND COBALT INTRINSIC ACTIVATOR

Example 7 was repeated except 1.0 ml 0.1M cobalt chloride was used the place of the cupric sulfate to form a propyl gallate/cobalt solution-form coagulation activator.

EXAMPLE 10

HEPARIN SENSITIVE INTRINSIC ACTIVATOR WITH PROPYL GALLATE, DEXTRAN SULFATE AND COPPER II

Example 7 was repeated except 1.0 ml 100 mg/dl dextran sulfate was added along with the cupric sulfate. A heparin sensitive coagulation activator with propyl gallate, dextran sulfate and copper was thus formed.

EXAMPLE 11

HEPARIN SENSITIVE INTRINSIC ACTIVATOR WITH PROPYL GALLATE, DEXTRAN SULFATE AND NICKEL

Example 8 was repeated except 1.0 ml 100 mg/dl dextran sulfate was added along with the nickel chloride to form a heparin sensitive coagulation activator containing propyl gallate, dextran sulfate and nickel.

EXAMPLE 12

HEPARIN SENSITIVE COAGULATION ACTIVATOR WITH PROPYL GALLATE, DEXTRAN SULFATE AND COBALT

The procedure of Example 9 was repeated except 1.0 ml 100 mg/dl dextran sulfate was added along with the cobalt chloride. A solution-form coagulation activator was thus formed which was sensitive to heparin and contained propyl gallate, dextran sulfate, and cobalt.

EXAMPLE 13

TANNIN AND COPPER II INTRINSIC ACTIVATOR 0.5 g tannin were dissolved in 1,000 ml reagent water. 1.0 ml 0.1M cupric sulfate were added whereafter the resulting solution was mixed for 10 minutes with a teflon coated stirring bar on a stir-plate. Then, 1.2 g TRIS buffer were added, and the resulting solution mixed for 10 minutes with a teflon coated stir-bar. A clear solution coagulation activator with tannin and copper was thus formed containing no visible suspended matter.

EXAMPLE 14

TANNIN AND NICKEL INTRINSIC ACTIVATOR

Example 13 was repeated except 1.0 ml 0.1M Nickel chloride was used in the place of the cupric sulfate thus forming a solution-form coagulation activator with tannin and nickel.

EXAMPLE 15

TANNIN AND COBALT INTRINSIC ACTIVATOR

Example 13 was repeated except 0.1 ml 0.1M cobalt chloride was used instead of the cupric sulfate. Also, 2,5 g HEPES hemi sodium salt were added instead of the TRIS, to thus make a coagulation activator in solution form containing tannin and cobalt.

EXAMPLE 16

HEPARIN SENSITIVE INTRINSIC ACTIVATOR WITH TANNIN, DEXTRAN SULFATE AND COPPER II

Example 13 was repeated, but 1.0 ml 100 mg/dl dextran sulfate was added along with the cupric sulfate to form a heparin sensitive coagulation activator solution containing tannin, dextran sulfate and copper.

EXAMPLE 17

HEPARIN SENSITIVE INTRINSIC ACTIVATOR WITH TANNIN, DEXTRAN SULFATE AND NICKEL

Example 14 was repeated except 1.0 ml 100 mg/dl dextran sulfate was added along with the nickel chloride. A heparin sensitive coagulation activator solution containing tannin, dextran sulfate and nickel was formed.

EXAMPLE 18

HEPARIN SENSITIVE INTRINSIC ACTIVATOR WITH TANNIN, DEXTRAN SULFATE AND COBALT

Example 15 was repeated, but 1.0 ml 100 mg/dl dextran sulfate was added along with the cobalt chloride to make a heparin sensitive coagulation activator with tannin, dextran sulfate and cobalt.

EXAMPLE 19

APTT REAGENT INCLUDING PROPYL GALLATE AND COPPER II ACTIVATOR

In this example, a solution-form aPTT reagent was formed which included a propyl gallate and copper coagulation activator. Accordingly, 0.5 g propyl gallate were dissolved in 1,000 ml reagent water. 1.2 g TRIS buffer were then dissolved in this solution whereafter it was mixed for 10 minutes with a teflon coated stirring bar on a stir-plate. 1.0 g Asolectin and 200 ml above solution were placed in a Waring blender and blended at full speed for 1.0 minute. The resulting emulsion was returned to the original solution and mixed for 10 minutes, whereafter 1.0 ml 0.1M cupric sulfate was added and the resulting solution was mixed for an additional 10 minutes. A solution-form aPTT reagent was formed which was clear and free from the cloudiness or suspended material commonly observed in commercial aPTT reagents.

EXAMPLE 20

APTT REAGENT CONTAINING PROPYL GALLATE AND NICKEL ACTIVATOR

Example 19 was repeated except 1.0 ml 0.1M nickel chloride was used instead of the cupric sulfate, thus forming a solution-form aPTT reagent containing a propyl gallate and nickel coagulation activator.

EXAMPLE 21

APTT REAGENT CONTAINING PROPYL GALLATE AND COBALT ACTIVATOR

Example 19 was repeated except 1.0 ml 0.1M cobalt chloride was used in the place of the cupric sulfate. A solution-form aPTT reagent containing a propyl gallate and cobalt activator was thus formed.

EXAMPLE 22

HEPARIN SENSITIVE APTT REAGENT CONTAINING DEXTRAN SULFATE AND A PROPYL GALLATE/COPPER II ACTIVATOR

The preparation of Example 19 was repeated except 1.0 ml 100 mg/dl dextran sulfate was added along with the cupric sulfate to render the aPTT reagent heparin sensitive. The reagent formed was a solution containing the propyl gallate/copper activator.

EXAMPLE 23

HEPARIN SENSITIVE APTT REAGENT CONTAINING DEXTRAN SULFATE AND A PROPYL GALLATE/NICKEL ACTIVATOR

Example 20 was repeated except 1.0 ml 100 mg/dl dextran sulfate was added along with the nickel chloride. Accordingly, a solution-form aPTT reagent was prepared which was sensitive to heparin and which contained a propyl gallate/nickel activator.

EXAMPLE 24

HEPARIN SENSITIVE APTT REAGENT CONTAINING DEXTRAN SULFATE AND A PROPYL GALLATE/COBALT ACTIVATOR

The preparation of Example 21 was repeated, but 1.0 ml 100 mg/dl dextran sulfate was added with the cobalt chloride. A solution-form aPTT reagent was formed containing a propyl gallate/cobalt coagulation activator and which was sensitive to heparin.

EXAMPLE 25

HEPARIN SENSITIVE APTT REAGENT CONTAINING DEXTRAN SULFATE AND AN ELLAGIC ACID/COPPER II ACTIVATOR 0.18 g tetramethylammonium hydroxide were dissolved in 1,000 ml reagent water. 0.034 g ellagic acid were dissolved in the tetramethylammonium hydroxide solution, after which 1.5 g phenol were dissolved in the tetramethylammonium hydroxide-ellagic acid solution. 1.0 g Asolectin and 200 ml of above solution were then added to a Waring blender and blended for 1 minute at top speed. The resulting emulsion was then returned to the original solution and mixed for 10 minutes with a teflon coated stirring bar on a stir-plate, whereafter 1.0 ml 0.1M cupric sulfate and 1.0 ml 100 mg/dl dextran sulfate were added and the resulting solution mixed for 10 minutes more. The resulting heparin sensitive aPTT reagent containing an ellagic acid/copper activator was a solution without any visible suspended material. Another identical reagent was prepared, except 1.2 g TRIS buffer were added in the final step.

EXAMPLE 26

HEPARIN SENSITIVE APTT REAGENT CONTAINING DEXTRAN SULFATE AND AN ELLAGIC ACID/NICKEL ACTIVATOR

Example 25 was repeated except 1.0 ml 0.1M nickel chloride was used in place of the cupric sulfate. A solution-form heparin sensitive aPTT reagent with an ellagic acid/nickel activator was thus prepared.

EXAMPLE 27

HEPARIN SENSITIVE APTT REAGENT CONTAINING DEXTRAN SULFATE AND AN ELLAGIC ACID/COBALT ACTIVATOR

Example 25 was repeated except 1.0 ml 0.1M cobalt chloride was used instead of the cupric sulfate to prepare a solution-form heparin Sensitive aPTT reagent with an ellagic acid/cobalt activator.

EXAMPLE 28

APTT REAGENT CONTAINING A TANNIN/COPPER II COAGULATION ACTIVATOR 0.5 g tannin were dissolved in 1,000 ml reagent water. 4.9 g HEPES 0.5 sodium were added to the resulting solution which was then mixed for 10 minutes with a teflon coated stirring bar on a stir-plate. 1.0 g Asolectin and 200 ml of the above solution were then placed in a Waring blender and blended at full speed for 1.0 minute. The resulting emulsion was returned to the original solution and mixed for 10 minutes. Thereafter, 1.0 ml 0.1M cupric sulfate was added and the solution mixed for another 10 minutes. Formed was an aPTT reagent in solution fore free from visible suspended materials, and containing a tannin/copper coagulation activator.

EXAMPLE 29

APTT REAGENT CONTAINING A TANNIN/NICKEL COAGULATION ACTIVATOR

Example 28 was repeated except 1.0 ml 0.1M nickel chloride was used instead of the cupric sulfate. A solution-form aPTT reagent was thus prepared having a tannin/nickel coagulation activator.

EXAMPLE 30

APTT REAGENT CONTAINING A TANNIN/COBALT COAGULATION ACTIVATOR

Example 28 was repeated except 1.0 ml 0.1M cobalt chloride was used instead of the cupric sulfate. A solution-form aPTT reagent was thus prepared having a tannin/cobalt coagulation activator.

EXAMPLE 31

HEPARIN SENSITIVE APTT REAGENT CONTAINING DEXTRAN SULFATE AND A TANNIN/COPPER II ACTIVATOR

Example 28 was repeated except 1.0 ml 100 mg/dl dextran sulfate was added along with the cupric sulfate. A heparin sensitive solution-form aPTT reagent was thus formed having a tannin/copper activator.

EXAMPLE 32

HEPARIN SENSITIVE APTT REAGENT CONTAINING DEXTRAN SULFATE AND A TANNIN/NICKEL ACTIVATOR

Example 29 was repeated except 1.0 ml 100 mg/dl dextran sulfate was added with the nickel chloride to form a heparin sensitive aPTT reagent containing a tannin/nickel activator and being in solution form.

EXAMPLE 33

HEPARIN SENSITIVE APTT REAGENT CONTAINING DEXTRAN SULFATE AND A TANNIN/COBALT ACTIVATOR

Example 30 was repeated, but with 1.0 ml 100 mg/dl dextran sulfate being added along with the cobalt chloride. A solution-form heparin sensitive aPTT reagent was thus formed including a tannin/cobalt coagulation activator.

EXAMPLE 34

INTRINSIC ACTIVATORS ARE IN SOLUTION

An amount of a coagulation activator of Example 2 was filtered through a 0.45 micron MILLIPORE filter, whereupon no residue on the filter was observed. Using the filtered coagulation activator, an aPCT test was performed on normal platelet rich plasma. The aPCT value using the filtered coagulation activator was 29.3 seconds. A similar aPTT was run using an unfiltered amount of the same coagulation activator, and a value of 29.4 seconds was obtained. It was thus demonstrated that the activator was in solution form.

EXAMPLE 35

SOLUTION FORM OF INVENTIVE aPTT REAGENTS 0.001 g of ASOLECTIN was reconstituted with 5 ml of the coagulation activator of Example 2. The resulting aPTT reagent was then filtered through a 0.45 micrometer MILLIPORE filter whereupon no residue was observed. An aPTT value of 27.2 for normal platelet rich plasma was obtained using the filtered reagent. Using a similarly prepared but non-filtered aPTT reagent, an aPTT value of 27.5 was obtained for normal platelet rich plasma, thus demonstrating that the total aPTT reagent is soluble.

While the inventions have been described in detail in the foregoing description, the same is to be considered as illustrative and not restrictive in character, it being understood that only the preferred embodiments have been described, and that all changes and modifications that come within the spirit of the invention are desired to be protected.

I claim:

1. A platelet-sensitive method for assaying blood coagulation, comprising the steps of:

incubating at least one sample of blood or of platelet-containing plasma derived therefrom, said sample being essentially free of platelet substitute, with a reagent containing a hydroxy-substituted aromatic compound and a metal ion in amounts effective and under conditions sufficient for said hydroxy-substituted compound to activate Hagemann factor and to cause the platelets in said sample to release Platelet Factor 3, wherein said hydroxy-substituted aromatic compound is selected from the group consisting of propyl gallate and tannin, or derivatives thereof capable of causing platelets to release Platelet Factor 3;

adding calcium to said sample to initiate clotting; and then measuring the time necessary for the sample to clot.

2. The method of claim 1 in which the hydroxy-substituted aromatic compound is propyl gallate.

3. The method of claim 1 wherein said sample is platelet rich plasma, whereby the method provides an activated plasma clotting time assay.

4. The method of claim 1 wherein said hydroxy-substituted aromatic compound is tannin.

* * * * *